(12) United States Patent
Nakamura et al.

(10) Patent No.: US 6,863,798 B2
(45) Date of Patent: Mar. 8, 2005

(54) METHOD OF PRODUCING WASHING, CLEANING AND STERILIZING SOLUTION AND SYSTEM USING SUCH SOLUTION

(75) Inventors: Shinichi Nakamura, Osaka (JP); Kunihiko Fukuzuka, Habikino (JP)

(73) Assignee: Omega Co., Ltd. (JP)

( * ) Notice: Subject to any disclaimer, the term of this patent is extended or adjusted under 35 U.S.C. 154(b) by 0 days.

(21) Appl. No.: 10/303,480

(22) Filed: Nov. 25, 2002

(65) Prior Publication Data

US 2003/0146108 A1 Aug. 7, 2003

(30) Foreign Application Priority Data

Dec. 28, 2001 (JP) ........................................ 2001-402070
Jun. 4, 2002 (JP) ........................................ 2002-163540

(51) Int. Cl.[7] ................................ B01J 8/00; B08B 3/00
(52) U.S. Cl. ...................... 205/687; 134/109; 204/232; 204/237; 205/516; 205/705
(58) Field of Search ................................ 205/705, 687, 205/516; 134/109; 204/232, 237

(56) References Cited

U.S. PATENT DOCUMENTS 5,205,994 A * 4/1993 Sawamoto et al. .... 422/186.07
6,251,258 B1 * 6/2001 Kojima et al. ............... 205/702
2003/0098244 A1 * 5/2003 Ruhr et al. .................. 205/516

FOREIGN PATENT DOCUMENTS

| JP | 58-067895 | * 4/1983 | ............. C25D/11/26 |
| JP | 60-243292 | * 12/1985 | ............. C25B/1/46 |
| JP | 05-269182 | 10/1993 | ............. A61L/2/18 |
| JP | 06-305866 | * 11/1994 | ............. C04B/41/90 |
| JP | 08-035087 | 2/1996 | ............. C25B/1/26 |
| JP | 08-132050 | 5/1996 | ............. C02F/1/46 |
| JP | 11-226092 | 8/1999 | ............. A61L/2/02 |
| JP | 2000-226680 | * 12/1999 | ............. C25B/1/26 |
| JP | 2000-198707 | 7/2000 | ............. A01N/59/08 |
| JP | 2001-232371 | 8/2001 | ............. C02F/1/50 |

* cited by examiner

Primary Examiner—Robert R. Koehler
(74) Attorney, Agent, or Firm—Hayes Soloway P.C.

(57) ABSTRACT

A washing, cleaning and sterilizing solution is produced by electrolyzing an electrolyte solution composed of mixed caustic soda and salt in an electrolyzer. The solution is used as it is or diluted with tap water or non-potable water. The solution is applicable to washing, cleaning and sterilizing metal goods, medical instruments, nursing products, foodstuff, farm products, marine products, dishes, cooking utensils, plastic goods, surrounding, facilities, fiber products, machine parts, machine goods, various containers, electrical communication components, vehicles, or the like.

10 Claims, 7 Drawing Sheets

RELATIONSHIP BETWEEN PH AND AMOUNT OF AVAILABLE CHLORIDE PRODUCED DURING ELECTROLYSIS OF NaCL SOLUTION: TWO-LITER 0.1% NaCL SOLUTION   ELECTROLYZING PERIOD: 30 MINUTES AVAILABLE CHLORIDE

RELATIONSHIP BETWEEN CONCENTRATION OF NaCL AND AMOUNT OF AVAILABLE CHLORIDE DURING ELECTROLYSIS OF NaCL SOLUTION:
2-LITER OF NaCL SOLUTION (PH 12.3)
ELECTROLYZING PERIOD: 30 MINUTES

CURVES OF OVA ADSORBED FROM SURFACES OF STAINLESS STEEL PARTICLES WASHED USING NaOH SOLUTIONS HAVING DIFFERENT pH VALUES

CURVES OF OVA ADSORBED FROM SURFACES OF STAINLES STEEL
PARTICLES WASHED USING NaOH SOLUTION, NaNO₃ ELECTROLYTE
AND NaCL ELECTROLYTE

♦: NANO₃ ELECTROLYTE
□: NaCL ELECTROLYTE

METHOD OF PRODUCING WASHING, CLEANING AND STERILIZING SOLUTION AND SYSTEM USING SUCH SOLUTION

BACKGROUND OF THE INVENTION

1. Field of the Invention

The present invention relates to a method of producing a cleaning, washing and sterilizing solution which is easily and effectively applied to industrial, household and environment fields in order to wash, clean and sterilize medical instruments, nursing products, foodstuff, farm products, marine products, dishes, cooking utensils, surrounds, facilities, fiber products, machine parts, machine goods, various containers, electrical communication components, vehicles and so on, and a washing, cleaning and sterilizing system using such a washing, cleaning and sterilizing solution.

2. Description of the Related Art

Organic solvents and detergents have been used in order to clean or wash fiber products, machine parts, machinery, various containers, electrical communication devices, vehicles and so on.

Detergents, organic solvents and so on have been generally used in order to clean or wash medical instruments, nursing products, foodstuff, farm products, marine products, dishes, cooking utensils, surrounds, facilities, fiber products, machine parts, machine goods, various containers, electrical communication components, vehicles and so on. However, some contaminants are too stubborn to be cleaned by detergents or to be extraction-cleaned by organic solvents. Further, removed contaminants are dissolved into the detergent or organic solvent. Such contaminated detergents or solvents have to be discarded as wastewater or waste fluid, which is a serious social problem.

The applicant has proposed (1) "Cleaning Water Producing Mechanism" in Japanese Patent Application No. H06-282247, in which a cleaning solution made of an electrolyzed sodium chloride or sodium bromide is used to clean and sterilize broilers, eggs, vegetables and so on without using any detergent. Although this mechanism is effective in removing blood or protein-related contaminants or stains compared with existing bleaches, it is not totally satisfactory.

Further, the applicant has proposed (2) "Sterile Washing Method for Medical Implement and Apparatus Therefore" in Japanese Patent Application No. H10-046239, in which an aqueous solution containing sodium chloride and potassium bromide at an appropriate concentration and inorganic acid is mixed and electrolyzed so as to have a pH value of 6 to 8. The obtained solution can sterilize medical instruments such as endoscopes, which are stained with spore forming bacteria. However, the solution suffers from a somewhat reduced effect on protein-related contaminants like blood, and tends to rust metal instruments.

Usually, a cleaning and sterilizing solution produced by electrolyzing a saline solution is very effective when it tends to the weak acid side. Therefore, salt is added during the electrolysis. However, it is difficult for such a solution to sufficiently clean and wash protein-related contaminants (such as blood, milk, secretions or the like), fat, oil and so on. An acidic electrolyte solution is effective in cleaning or washing, but has a problem of causing metallic corrosion, and has not been widely applied to cleaning, washing and sterilizing metallic medical instruments, vehicles, machinery, machine components and so on.

The present invention has as an object to overcome the foregoing problems related to cleaning, washing and sterilizing of medical instruments, nursing products, foodstuff, farm products, marine products, dishes, cooking utensils, surrounds, facilities, fiber products, machine parts, machine goods, various containers, electrical communication components, vehicles and so on. The invention provides a method and a device for cleaning, washing or sterilizing the foregoing objects through oxidation decomposition without using detergents, organic solvents or the like.

The washing, cleaning and sterilizing solution is re-electrolyzed and purified, and can be repeatedly used without refilling fresh water. The solution can wash, clean and sterilize objects without generating any wastewater or waste fluid.

Even if an electrolyte solution contains chloride ions, it can be electrolyzed without generating any chloride gases which are harmful to eyes or skin, or cause corrosion or rust on metal objects. Further, if the electrolyte solution is mild alkali, it is as effective as or more effective than an electrolyte solution containing hypochlorous soda, active oxygen and so on. The invention intends to provide a method and device for producing a washing, cleaning and sterilizing solution that is applicable to a variety of fields, and is easy and inexpensive to produce.

SUMMARY OF THE INVENTION

The invention aims at providing a method and device in order to accomplish the foregoing objects.

There is provided a method of producing a washing, cleaning and sterilizing solution, comprising electrolyzing an electrolyte solution composed of mixed caustic soda and salt and producing a washing, cleaning and sterilizing solution, and determining whether to use the produced solution as it is or to dilute it with tap water or non-potable water.

The washing, cleaning and sterilizing solution, which is produced by electrolyzing a solution composed of mixed caustic soda and salt using an electrolyzer 1, is filled in a washing bath 8 or a washing machine 9 either with or without being diluted with tap water or non-potable water. Small items such as metal goods, fiber products, plastic goods or the like are put into a basket, and immersed, washed and sterilized in the washing bath 8 or the washing machine 9. When a number of items are continuously washed, they may be transported on a conveyer. Fiber produces contaminated with blood may be conveniently washed using a washing machine.

The electrolyte is an alkali group electrolyte containing caustic soda, caustic potash, hypochlorous soda or the like, a neutral salt group electrolyte containing salt, potassium chloride, sodium bromide, potassium bromide, sodium nitrate and so on, a solution including both an alkali group electrolyte and a neutral salt group electrolyte, or a solution including at least one of substances of either an alkali or neutral salt group electrolyte. Further, it is possible to produce a washing, cleaning and sterilizing solution by electrolyzing a solution composed of at least one of the foregoing substances, although such a solution may have effects somewhat different from those of the foregoing solution of the present invention.

It is preferable that the washing, cleaning and sterilizing solution, which is produced in the electrolyzer 1 by mixing an alkali group electrolyte solution containing caustic soda and so on with a neutral salt electrolyte solution containing salt, potassium chloride, sodium bromide, potassium bro mide and so on, has a pH value of 8 to 13. The washing, cleaning and sterilizing solution preferably has a pH value of 10 to 12.3 in order to promote sterilization and protect metal goods and metal parts against rust.

The washing, cleaning and sterilizing solution may be sprayed onto contaminated metal goods, fiber products, plastic goods or the like when they are too large. Further, spraying the solution is effective in washing, cleaning and sterilizing vehicles, aircrafts, construction machine, beds and operating room tables in hospitals, floors, fish markets, cooking tables for the food industry, and so on.

The washing, cleaning and sterilizing solution may be injected into contaminated tanks, devices or fluid circulating pipes 12, thereby cleaning, washing and sterilizing inner surfaces thereof.

The used washing, cleaning and sterilizing solution is re-electrolyzed by the electrolyzer 1, and is subject to anodic oxidation in order to decompose contaminants dissolved therein. Specifically, the used solution is returned from the washing tank 8 or the washing machine 9 to the electrolyzer 1 by a circulating pump 11 via the fluid circulating pipe or the like 12, is re-electrolyzed by the electrolyzer 1, is subject to decomposition of contaminants by anodic oxidation, and is used repeatedly. The revived solution may be repeatedly supplied to metal or plastic pipes of the circulating path 12 of the washing bath 8 or washing machine 9, tanks, water heaters, boilers, heat exchangers, and non-potable water paths of cooling towers.

In the electrolyzer 1, the anode 13 is made of a conductive metal which is covered with a conductive ceramics film, a vacuum-evaporated or thermal sprayed conductive ceramics film, or with a diamond film which is made conductive and is vacuum-evaporated or thermal sprayed, and the cathode 14 is made of a conductive material such as titanium, stainless steel or the like. The electrolyte solution is supplied between the anode 13 and the cathode 14. The foregoing anode has a very long life. Alternative, the anode may have another structure. Since the electrolysis is performed using the alkali electrolyte solution, a platinum-plated anode and cathode may be also usable.

The electrolyte solution is made by mixing a solution composed of caustic soda, caustic potash, hypochlorous soda or the like with a saline solution containing potassium chloride, and is stored in the electrolyte solution container 2. The electrolyte solution is supplied to the electrolyzer 1 by a fixed capacity pump 3, and is electrolyzed by the electrolyzer 1. The electrolyte solution is used as it is or is diluted with tap water or well water, and is filled into the washing bath 8 or the washing machine 9, and is used to wash and sterilize stained metal goods, fiber products, plastics goods or the like.

According to the first aspect of the invention, the electrolyte solution is produced by electrolyzing an alkali caustic acid solution and a neutral saline solution. The electrolyte solution is used as it is or diluted by tap water or non-potable water. The electrolyte solution produced by adding salt to the alkali solution and having a high pH value can more effectively sterilize bacteria than neutral to weakly acidic electrolytes.

The washing, cleaning and sterilizing solution is very effective in cleaning and washing protein-related contaminants (such as blood, milk and so on), which coagulate in response to acid.

The alkali electrolyte solution assures high sterilizing performance, and can effectively clean and wash fat, fatty oil, mineral oil, and so on.

The invention is effective in cleaning, washing and sterilizing the following contaminants using a washing machine compared with the related art: protein-related contaminants (e.g. blood, milk and so on), as well as fat, fatty oil, mineral oil and so on. These contaminants can be washed away without using any detergent or with only a small quantity of detergent. The sterilizing solution including the dissolved contaminants is subject to the oxidation decomposition, purified, and can be repeatedly used. Therefore, substantially little or no wastewater is generated. Sheets, white dresses and so on which are stained or contaminated by blood, pus, medicines or the like at hospitals can be cleaned, washed and sterilized at the same time.

The cleaning, washing and sterilizing solution can wash and sterilize medical instruments that suffer from protein-related contaminants (such as blood, pus, medicines and so on). The solution is alkali, and can protect metal instruments against corrosion and rust.

Further, the cleaning, washing and sterilizing solution is applicable to washing and sterilizing foodstuff, fish and seafood, vegetables, fruits, beef, pork, chicken meat, and eggs as described above.

The solution is also effectively applied to cleaning of metal components, which are contaminated with fat, fatty oil or mineral oil when they are being machined. Further, the washed goods are resistant to rust compared with goods that are washed by existing detergents or organic solvents.

In a second aspect of the present invention, the cleaning, washing and sterilizing solution is produced by electrolyzing a mixed caustic soda and salt by the electrolyzer 1. The solution is used as it is or is diluted by non-potable water, and is poured into the washing bath 8 or washing machine 9. The objects to be cleaned are placed into the washing bath 8 or washing machine 9, and are immersed and washed therein. Small objects like metal goods, plastic products and so on are placed directly into the washing bath 8 or are placed therein using a basket. A conveyor may be used when objects are washed one after another. Spraying the cleaning, washing and sterilizing solution may clean large objects. Fiber products stained or contaminated with blood can be conveniently washed using a washing machine.

Although an electrolyte solution containing chloride ions is electrolyzed, no chloride gas harmful to eyes and skin will be generated. Further, the electrolyte solution does not corrode or affect the quality of metal goods. Further, the alkali electrolyte solution is as effective as or more effective than mildly acidic electrolyte solution containing hypochlorous acid and active oxygen.

The cleaning, washing and sterilizing solution can wash and sterilize medical instruments, nursing products, foodstuff, farm products, marine products, dishes, cooking utensils, surrounds, facilities, fiber products, machine parts, machined products, various containers, electrical communication components, vehicles and so on, without using detergents or organic solvents. Further, the solution can clean and wash oily stains or contaminants or stubborn protein-related stains or contaminants through oxidation decomposition without using detergents, organic solvents and so on.

In accordance with a third aspect of the invention, an alkali electrolyte solution prepared by electrolyzing a solution containing bromide ions and chloride ions produces hydro halogen acid and remains stable, and can demonstrate sufficient cleaning, washing and sterilizing performance due to strong oxidation caused by active oxygen such as super oxide ions and hydroxyl radicals.

According to the fourth aspect of the invention, the washing, cleaning and sterilizing solution is produced by mixing an alkali group electrolyte solution containing caustic soda, caustic potash or like with the neutral salt electrolyte solution containing salt, potassium chloride, potassium bromide and so on. When the solution has a pH value of 10 to 12.3, it can protect metal products and metal components against rust. Further, the alkali electrolyte solution is electrolyzed, so that the electrolyzer is protected against corrosion. Any kind of electrolyzer can enjoy a longer effective life.

According to the fifth aspect of the invention, the cleaning, washing and sterilizing solution can be sprayed onto stained or contaminated metal goods, fiber products, plastic goods and so on in order to clean, wash and sterilize them, and is applicable to large objects such as machinery, vehicles and aircrafts.

According to a sixth aspect of the invention, the cleaning, washing and sterilizing solution can be injected into stained or contaminated tanks, fluid processing lines or the like. Specifically, the solution is preferable in the cleaning and washing of inner surfaces of processing lines of mineral oil, fat and fatty oil, oil and fatty products, milk, diary products, storage tanks, piping systems, or transportation systems like tank trucks, containers, drums and so on.

According to a seventh aspect of the invention, the used cleaning, washing and sterilizing solution is returned to the electrolyzer 1 by the circulating pump 11 via the circulation path 12, and is re-electrolyzed by the electrolyzer 1. Stains or contaminants dissolved into the solution are subject to the anodic oxidation and decomposition. Therefore, the solution can be repeatedly used, which is effective in tremendously reducing an amount of water to be used and obviating wastewater.

According to an eighth aspect of the invention, in the electrolyzer 1, the anode 13 is made of a conductive metal which is covered with a conductive ceramics film, a vacuum-evaporated or flame-sprayed conductive ceramics film, or with a diamond film which is made conductive and is vacuum-evaporated or thermal sprayed, and a cathode 14 is made of a conductive material such as titanium, stainless steel or the like. For the electrolysis, the electrolyte solution is supplied between the anode and the cathode, both of which is resistant to high current density and have long life.

Since the electrolysis can be performed using high current density, the cleaning, washing and sterilizing solution is applicable to metal goods, fiber products, plastics having stubborn stains or contaminants caused by dioxins, agricultural chemicals or earth, which are difficult to decompose. Further, the solution is effectively applicable to cleaning, washing and sterilizing of *Helicobacter pylori* and spore forming bacteria which are carried on endoscopes or surgical operation instruments and which have been very difficult to sterilize up to now, and can reliably sterilize endoscopes and surgical operation instruments. Since the electrolyte solution is alkali, it can protect metal medical instruments against corrosion and rust.

According to a ninth aspect of the invention contaminated goods are immersed and cleaned, washed and sterilized in the washing bath 8 or the washing machine 9 filled with the washing, cleaning and sterilizing solution which is composed of an alkali group electrolyte solution produced by electrolyzing an electrolyte solution composed of mixed caustic soda, caustic potash, hypochlorous soda or the like, a neutral salt group electrolyte solution containing salt, potassium chloride, sodium bromide, potassium bromide or the like, the electrolyte solution including both an alkali group electrolyte and a neutral salt group electrolyte, or the electrolyte solution including at least one of substances of either an alkali or neutral salt group electrolyte. The electrolyte solution is used as it is or is diluted by tap water or non-potable water. Stained metal goods, fiber products, plastics goods or the like are immersed, cleaned, washed and sterilized in the washing bath 8 or the washing machine 9.

Stained or contaminated medical instruments, nursing products, foodstuff, agricultural products, machine products, dishes, cooking utensils, fiber products machine components, and so on can be cleaned, washed and sterilized by diluting the electrolyte solution with tap water or well water. Oily stains or contaminants and protein-related stubborn stains or contaminants can be cleaned and washed by the oxidation decomposition without using any detergent and organic solvents.

The used solution can be purified and repeatedly used, which is effective in obviating wastewater or waste fluid.

DESCRIPTION OF THE PREFERRED EMBODIMENTS

Figure 1:
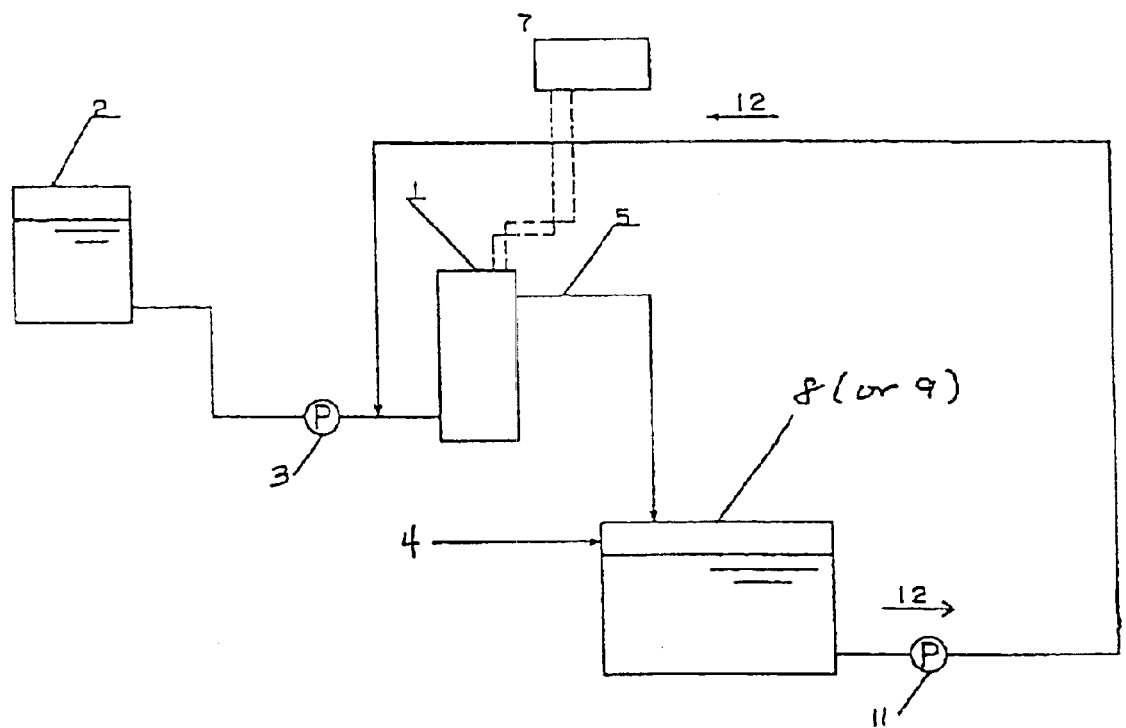
FIG. 1 is a flow sheet of a washing, cleaning and sterilizing process.

The invention will be described with reference to embodiments shown in the drawings. Referring to FIG. 1, an electrolyte solution container 2 stores an electrolyte solution composed of a solution containing caustic soda, hypochlorous soda or the like, or an electrolyte solution containing the foregoing solution in which salt or potassium chloride is dissolved. The electrolyte solution is supplied to an electrolyzer 1 by a fixed capacity pump 3, is electrolyzed by the electrolyzer 1, and has tap water or non-potable water 4 added, so that a cleaning, washing and sterilizing solution is produced. The washing, cleaning and sterilizing solution is transmitted via a washing, cleaning and sterilizing solution path 5 to a washing bath 8 or a washing machine 9, which is provided with a stirrer or an ultrasonic generator 32, and is used to clean or wash objects.

The used washing, cleaning and sterilizing electrolyte solution is returned to the electrolyzer 1 by a circulating pump 11 via a circulating path 12 or the like, and is re-electrolyzed by the electrolyzer 1, so that contaminants dissolved into the solution are decomposed by the anodic oxidation. Therefore, the revived solution can be repeatedly used.

Embodiment 1

Figure 2:
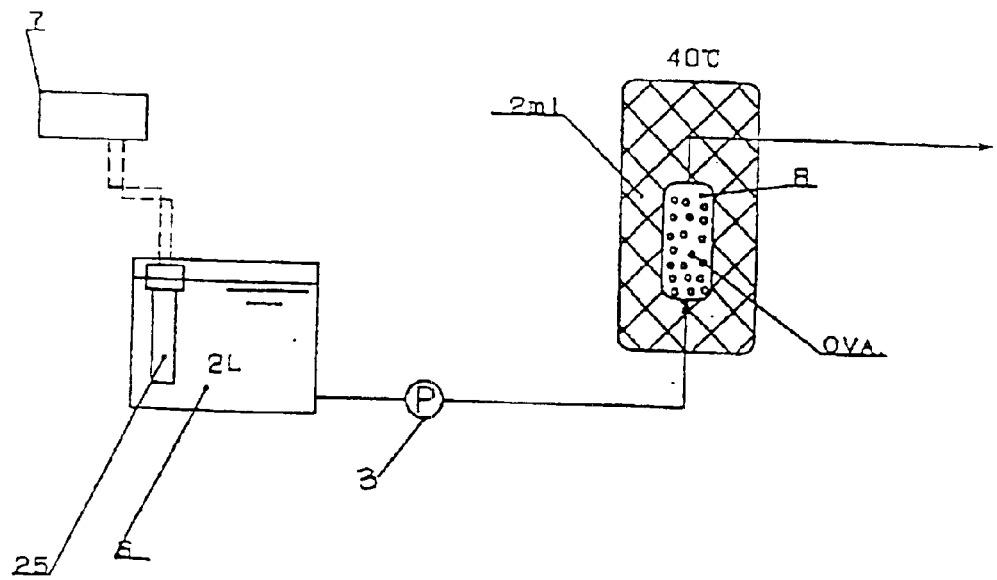
FIG. 2 is a flow chart showing a cleaning/washing experiment.
Figure 3:
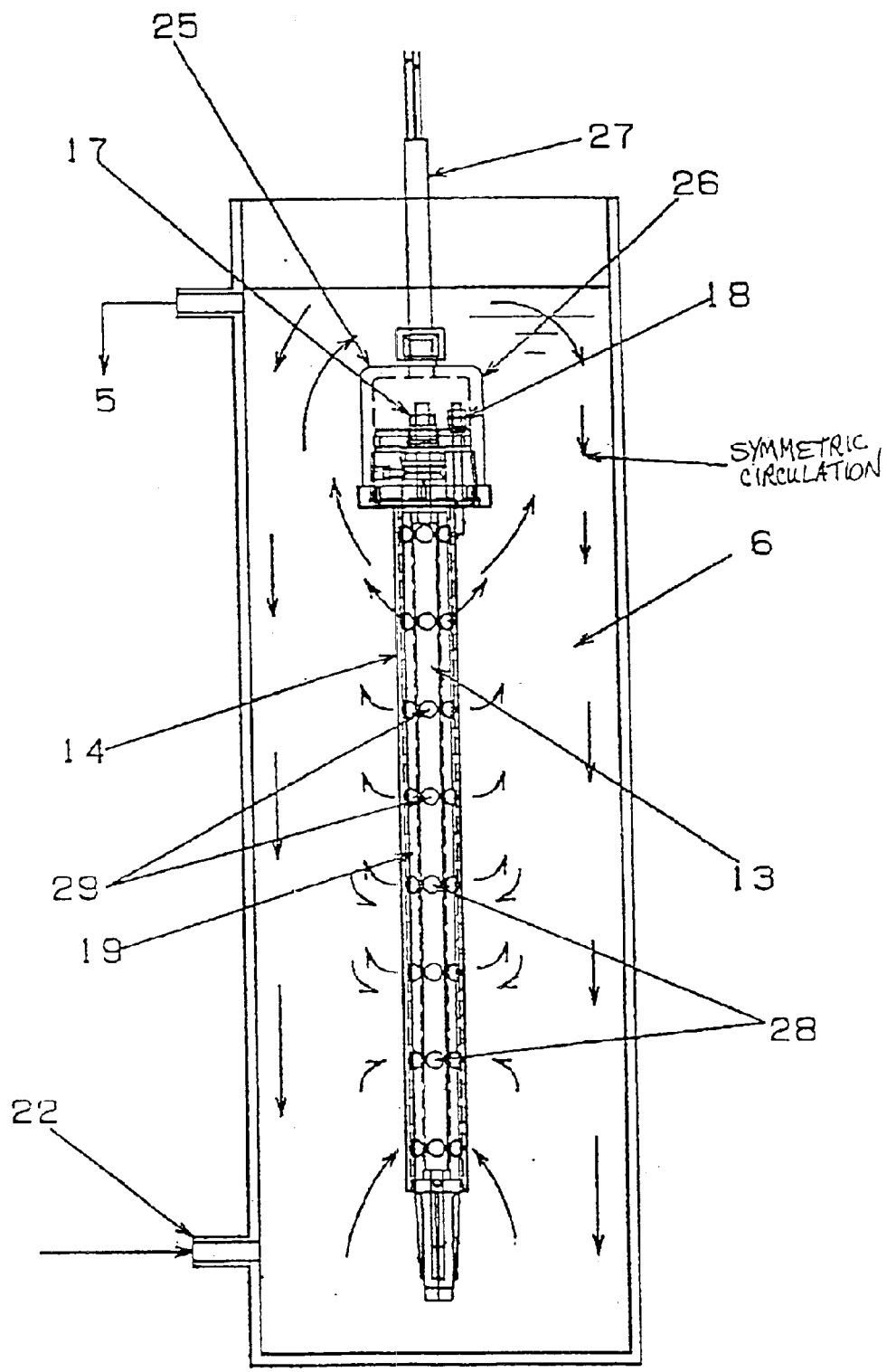
FIG. 3 is a cross section of an immersion type electrolyzer which includes an anode and a cathode, and is immersed in a sterilizing solution reservoir 6.

Up to now, chlorinated alkali detergents of hypochlorous soda group have been used for cleaning or washing protein-related stains or contaminants, but have not always removed them sufficiently. In order to overcome this problem, a 2-liter electrolyte solution prepared by adding caustic soda to a saline solution and having a pH value of 9 to 13 is stored in the electrolyte solution container 6, in which an immersion type electrolyzer 25 is directly placed, and electrolyzes the electrolyte solution. FIG. 2 is the chart showing an experimental cleaning process, and FIG. 3 is the cross section of the immersion type electrolyzer 25.

The following model specimens were used as protein-related stains or contaminants: fine stainless steel particles 21 (SUS3161L, produced by Nirako Co., Ltd.) having a surface area of 0.12 $m^2/g$; and egg-white albumin (OVA, produced by Sigma Co., Ltd.). During experiments, a 50-ml OVA solution (3 g/l) and fine stainless steel particles 21 were put into a 125-ml glass vial at 80° C. for two hours, so that the OVA solution was in osmotic contact with the stainless steel particles 21. The OVA in the amount of 8.8 $mg/m^2$ stuck onto the stainless steel particles 21. Thereafter, the stainless steel particles 21 were sufficiently washed by water, and were dried for 24 hours at 40° C.

Figure 4:
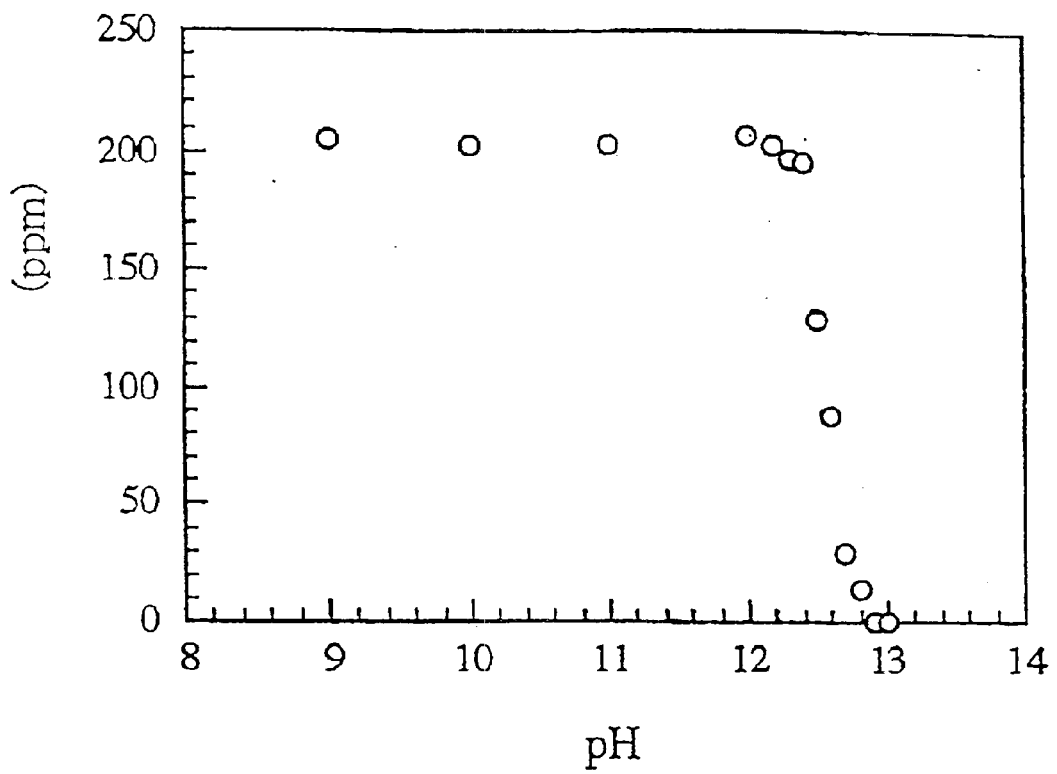
FIG. 4 is a graph showing the relationship between pH and an amount of available chloride produced during electrolysis of NaCl.

A 2-ml cleaning glass cylinder 8 was maintained at 40° C., and was filled with the 2-g OVA-stained stainless steel particles 21. An electrolyte solution containing a NaOH electrolyte solution (pH 12 to 13.5) and a NaCl electrolyte solution were supplied to the cleaning glass cylinder 8 via a bottom thereof (at a rate of 1 ml/min), thereby washing the stainless steel particles 21. FIG. 4 shows the relationship between a pH value of the NaCl electrolyte solution and a concentration of available chloride (residual chloride) when 0.1% NaCl electrolyte solution was electrolyzed for 30 minutes.

The concentration of available chloride was 201 mg ±5 mg for pH 9 to 12.4, and remained substantially unchanged. Further, the concentration remained at the same value after the electrolyte solution was left for 24 hours (at room temperature).

If the electrolyte solution had a pH value of 12.5 to 13.0, which was higher than pH 9 to 12.4, the amount of available chloride was extensively decreased as the pH value was raised. With pH 13.0, no available chloride was recognized even if a concentration of salt was increased to 0.5% from 0.1%.

Figure 5:
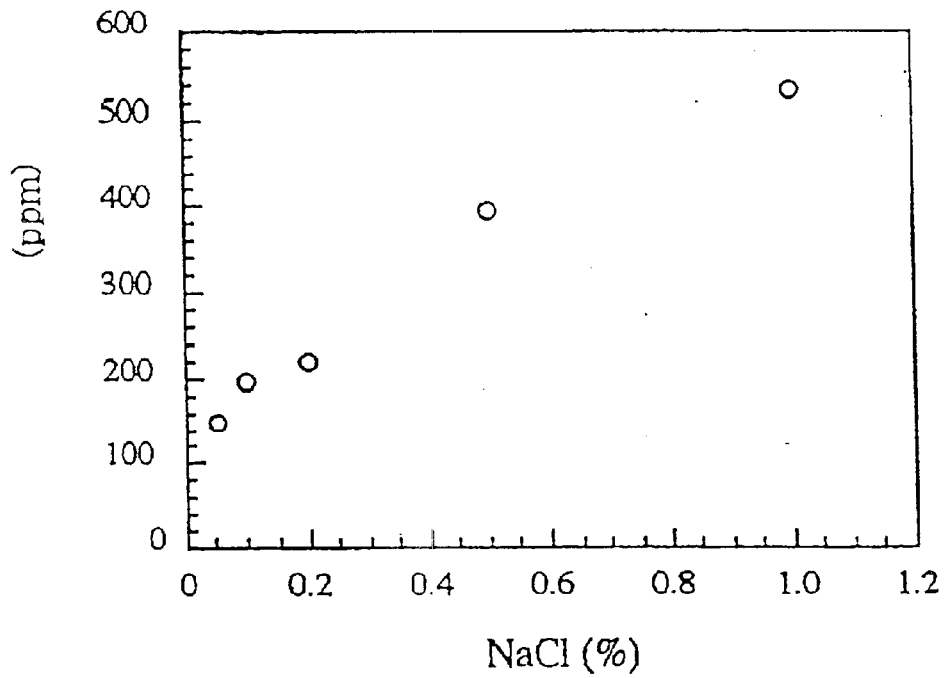
FIG. 5 is a graph showing the relationship between the amount of available chloride, which is produced during electrolysis of NaCl, and concentration of NaCl.

FIG. 5 shows the relationship between an amount of available chloride and an initial NaCl concentration after a saline solution with pH 12.3 was electrolyzed (for 30 minutes). The available chloride increased as NaCl was concentrated. The available chloride concentration reached 530 mg/l in a 1.0% saline solution.

Figure 6:
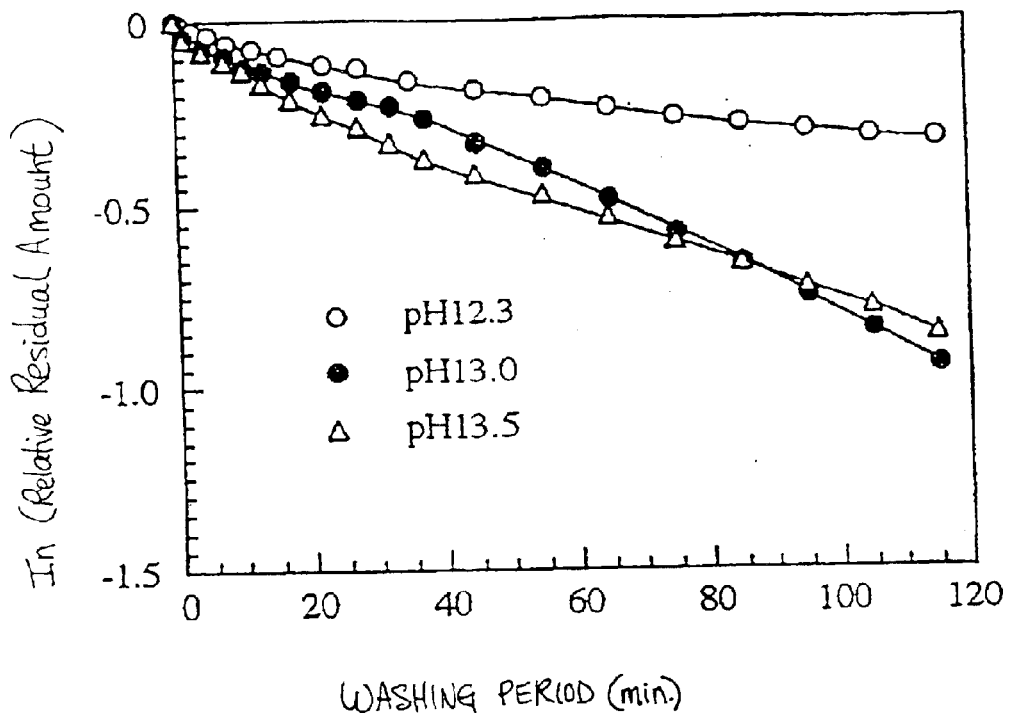
FIG. 6 is a graph showing desorption curves of OVA (egg white albumin) adsorbed from surfaces of stainless steel particles washed using NaOH solutions having various pH values.

The OVA (egg-white albumin) contains a free thiol group (—SH group) in molecules thereof, and becomes very difficult to clean or wash due to thermal degeneration when it is heated to 78° C. or higher. FIG. 6 shows the desorption curves of the OVA adsorbed from the stainless steel particles washed using NaOH solutions having different pH values. The abscissa represents a cleaning period while the ordinate represents the natural logarithm of a relative residual amount of the OVA. In the semi-logarithmic graph of FIG. 6, the cleaning curves can be approximated to straight lines at several points, so that it is not possible to assume that simple primary desorption has occurred. A desorption rate at pH 12.3 is lower than a desorption rate at pH 13, but a desorption rate at pH 13 is equal to or lower than a desorption rate at pH 13.5 (i.e. pH 12.3<pH 13 pH 13.5). Cleaning efficiency depends upon pH (concentration of OH).

Figure 7:
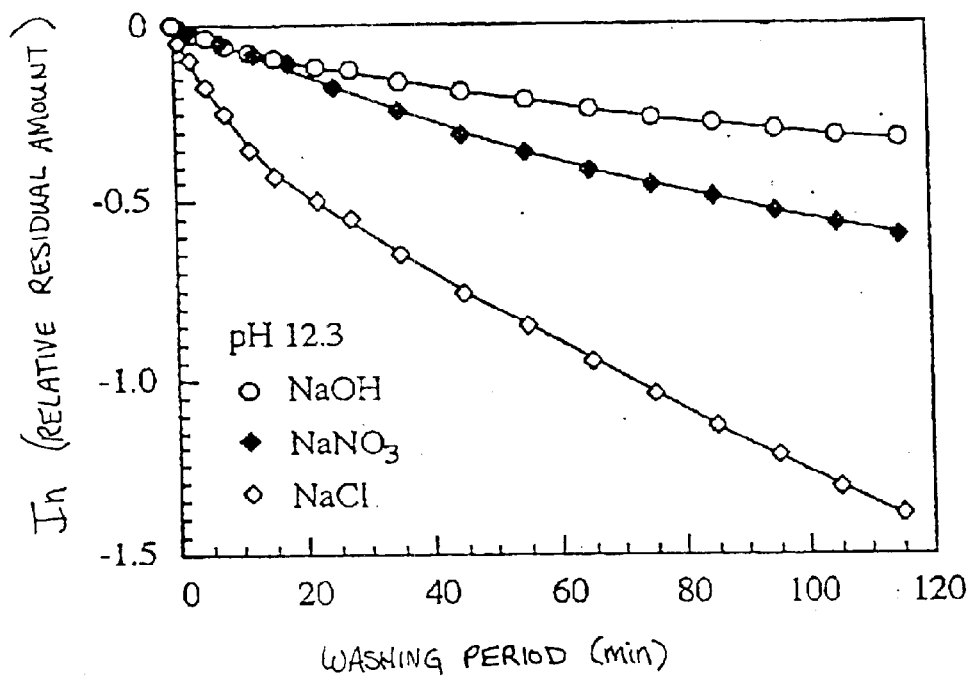
FIG. 7 is a graph showing desorption curves of OVA adsorbed from surfaces of stainless steel particles washed using a NaOH solution, a $NaNO_3$ electrolyte solution, and a NaCl electrolyte solution.

FIG. 7 shows comparison experiments of a NaCl electrolyte solution, a $NaNO_3$ electrolyte solution and a NaOH electrolyte solution, each of which had pH 12.3, was used to clean and wash OVA-stained stainless steel particles. The Na $NO_3$ electrolyte solution adsorbed and cleaned the OVA slightly faster than the NaOH electrolyte solution. The Na $NO_3$ electrolyte solution seems to be effective since active oxygen species were produced by the electrolysis.

On the other hand, the NaCl electrolyte solution (having the concentration of available chloride of 200 mg/l) adsorbed the OVA much faster than the Na $NO_3$ electrolyte solution and the NaOH electrolyte solution.

Embodiment 2

Generally speaking, dedicated laundries collect white dresses, sheets and so on from hospitals, on a weekly or bi-weekly basis and clean and wash them using detergents and bleaches. With lapse of time, blood, medicines or the like which stain or contaminate white dresses or sheets become very difficult to cleaned or bleach using ordinary detergents or bleaches when they are washed in usual ways. Therefore, such white dresses or sheets often tend to be discarded. In a second embodiment of the invention, white dresses or sheets to be discarded were cleaned and washed using an electrolyte solution composed of hypochlorous soda, salt and sodium bromide, according to the process shown in FIG. 1.

Cleaning was conducted using an automatic washing machine, which was manufactured by Sharp Co., Ltd., had a standard water quantity of 37 liters, and was of swirl and instant reversal type. An anode 13 was made of platinum-plated titanium while a cathode 14 was made of titanium. The anode 13 and cathode 14 were spaced 4 mm apart. An electrolyte solution was produced by electrolyzing dissolved 12% hypochlorous soda, available on the market, 3.2% salt and 0.8% sodium bromide (NaCl:NaBr=8:2), and was diluted 450 times with water. The diluted electrolyte solution had electric conductivity of 1800 $\mu s/cm$, and a concentration of available chloride of 280 mg/l. When electrolyzed using a 12A current for 10 to 20 minutes, the electrolyte solution had a concentration of available chloride which was increased to 280 mg/l to 340 mg/l.

Approximately 2 kg cloth torn from white dresses, sheets or the like stained or contaminated by blood, medicine and so on was immersed and stirred in a washing machine which contained 20-liters of tap water. At first, 5-liters of electrolyte solution having a concentration of available chloride of 340 mg/l was poured into the washing machine and was stirred for five minutes. Then another 5-liters of electrolyte solution was poured into the washing machine and was stirred for five minutes. The cleaned and washed objects were rinsed and dried. They were compared with objects which were washed using detergents and bleaches. The objects washed by the electrolyte solution were freed from blood, medicine or other stains, and were completely whitened. Substantially all of the original stains or contaminants remained on the normally washed objects.

Embodiment 3

In a third embodiment, caustic soda was added to 5-liters of pure water using the electrolyte solution container 2 (shown in FIG. 1), to obtain a caustic soda electrolyte solution having pH 12, to which a 0.1% saline solution (pH 12) was added. The caustic soda electrolyte solution and 0.1% saline electrolyte solution were continuously electrolyzed for 10 minutes by the electrolyzer 1, and were poured into the washing bath 8. Five compressor components (i.e. cast iron components having a 10 mm diameter and 15 cm length) were suspended using strings and were immersed in the caustic soda electrolyte solution and 0.1% saline electrolyte solution which were in the washing bath 8. The solutions were stirred by a stirrer 32 at the bottom of the washing bath 8 and washed the compressor components for 15 minutes. The washed components were then dried by compressor air.

For comparison, another group of compressor components was washed in the washing bath 8 using a caustic soda solution (pH 12) and an alkali detergent for 15 minutes. Average fat and fatty oil sticking onto un-washed compressor components and fat and fatty oil on the washed compressor components were ultrasonic-extracted for three hours using a chlorofluorocarbon (Fureon 141b liquid). The extracts were sucked and filtered by a glass filter (GA55 of ADVANTEC), and filtrates were heated and condensed on a hot plate, thereby obtaining fat and fatty oil contents. Solids were separated from the fat and fatty contents, which were dried again. The washed compressor components were left in a room for one month, and were checked with respect to rust. Table 1 shows the result of the foregoing experiment.

concentration of active and available chloride. Further, stains or contaminants dissolved into the sterilizing solution are purified by anodic oxidation and decomposition. The sterilizing solution in the reservoir 6 is sprayed using a spray nozzle 31 onto large objects such as operating tables, which cannot be washed in a washing bath 8.

Embodiment 5

Figure 9:
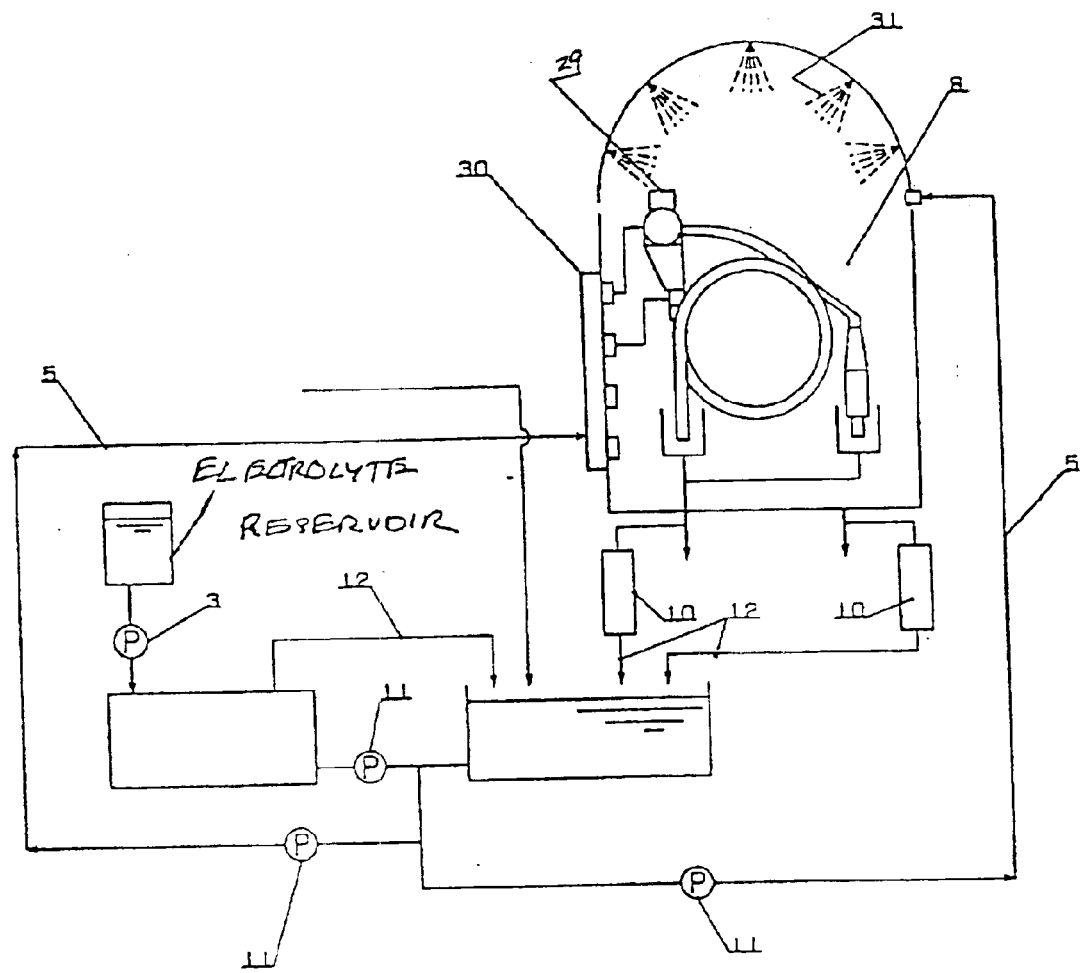
FIG. 9 shows a cleaning, washing and sterilizing system for endoscopes.

FIG. 9 shows a cleaning, washing and sterilizing system for endoscopes. A washing tube is connected to a sterilizing solution supplying joint 30 in order to supply a sterilizing solution into a forceps tube of the endoscopes. In this state, the endoscopes are cleaned, washed and sterilized. The used sterilizing solution is drained as a waste fluid, or is returned to the electrolyzer 1 via the circulating path 12, is re-electrolyzed, subject to anodic oxidation and decomposition by the electrolyzer 1, and used repeatedly. The external surface of the endoscopes is cleaned, washed and sterilized by the sterilizing solution injected by the spray nozzle 31 connected to the sterilizing solution supply path 5.

In this embodiment, an (Olympus Q10) endoscope was exposed to a 24 hour proliferating cultivation of *E. coli* in Heart Infusion Broth (HIB). The endocope was immersed for five minutes, and then removed. A bacteria containing solution in the amount of 20 ml was injected into the endoscopes via the forceps tube thereof, and the endoscope

TABLE 1

|  | Solid (mg) | | Oil content (mg) | | Rust | |
| --- | --- | --- | --- | --- | --- | --- |
|  | Alkali detergent (related art) | Alkali electrolyzed solution (present invention) | Alkali detergent (related art) | Alkali electrolyzed solution (present invention) | Alkali detergent (related art) | Alkali electrolyzed solution (present invention |
| Before cleaning |  | 13.4 |  | 26.6 |  | None |
| After cleaning | 9.5 | 5.4 | 6.3 | 2.4 | Completely rusted | Partially & lightly rusted |

Embodiment 4

Figure 8:
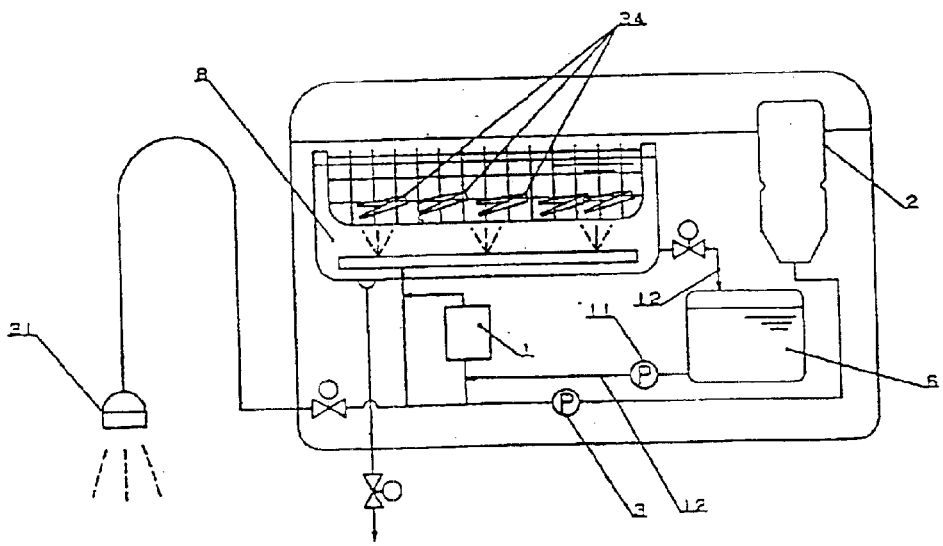
FIG. 8 shows a cleaning, washing and sterilizing system for medical instruments.

FIG. 8 shows a washing, cleaning and sterilizing system applicable to medial instruments. Such a system is used for cleaning, washing and sterilizing protein-related stains or contaminants (e.g. blood, pus, medicines and so on) on metal instruments for surgical operation (such as surgical knives, tweezers, catheters and forceps), needle therapy and cauterization instruments, contact lenses and dental surgical instruments. Surgical operation instruments and so on are placed in a stainless steel basket, which is immersed in an electrolyzed sterilizing solution in the washing bath 8, and is washed therein. A caustic acid solution (i.e., an alkali electrolyte) and a saline solution (i.e. a neutral electrolyte) are mixed, stored in the electrolyte solution container 2, supplied to the electrolyzer 1 by the quantitative pump 3, and injected into the washing bath 8 as the electrolyzed sterilizing solution.

The electrolyzed sterilizing solution is stored in the sterilizing solution reservoir 6. The sterilizing solution is returned to the electrolyzer 1 by the circulating path 12 and circulating pump 11, and is repeatedly electrolyzed after or during the sterilization in order to maintain a required was left standing for 10 minutes. After that, the endoscope was exposed to HIB in the amount of 20 ml and air in the amount of 20 ml, and was bacteria-stained.

The cleaning, washing and sterilizing system for five minutes washed the endoscope, and had the external surface thereof wiped using a sterilized cotton swab. The wiped bacteria in the amount of 5 ml were made to float in the HIB, which was gradually diluted. The diluted HIB in the amount of 10 μl was added to 80 μl HIB. The bacteria in the HIB were aerobically cultured in a micro plate at 37° C. for 24 hours. Thereafter, the presence of bacteria cultured on the bottom of the micro plate was checked by visual observation.

The HIB in the amount of 20 ml was poured into the forceps tube in order to wash away the bacteria remaining therein. Finally, 10 ml HIB discharged from the endoscope was gradually diluted in order to culture bacteria. The bacteria cultured at the bottom of the micro plate were collected as described above, and checked by the visual observation. Table 2 shows the results of the experiment.

TABLE 2

| Cleaning solution | Exterior of endoscope | | Interior of endoscope | |
|---|---|---|---|---|
| | 1 minute | 5 minutes | 1 minute | 5 minutes |
| Electrolyzed sterilizing solution | $1.5 \times 10$ | — | $1.2 \times 10$ | — |
| Tap water | $8.6 \times 10^4$ | $4.7 \times 10^2$ | $5.2 \times 10^6$ | $3.8 \times 10^5$ |
| 2.5% Glutaralclenide (Johnson & Johnson CIDEX) | $6.4 \times 10$ | — | $58 \times 10^2$ | $2.3 \times 10$ |

The invention has been described with respect a number of embodiments, but this is not limiting, and various modifications are possible without departing from the spirit and scope of the invention as defined in the attached claims.

What is claimed is:

1. A method of producing a washing, cleaning and sterilizing solution, comprising:

electrolyzing an alkaline electrolyte solution having a pH value of 8 to 13 and composed of mixed caustic soda and sodium chloride using an electrolyzer whereby to produce a concentrated a washing, cleaning and sterilizing solution;

using the produced solution as it is or diluted with tap water or non-potable water; and returning used washing, cleaning and sterilizing solution to the electrolyzer, where the solution is re-electrolyzed and contaminants contained therein decomposed by anodic oxidation.

2. A method of washing or cleaning metal goods, fiber products, plastic goods or the like, comprising:

filling a washing bath or a washing machine with a washing, cleaning and sterilizing solution which is produced by electrolyzing an electrolyte solution composed of mixed caustic soda and salt as defined in claim 1, the produced washing, cleaning and sterilizing solution being used as it is or diluted with tap water or non-potable water;

immersing and washing items to be cleaned, washed and sterilized in the washing bath or the washing machine; and returning used washing, cleaning and sterilizing solution to the electrolyzer, where the solution is re-electrolyzed and contaminants contained therein decomposed by anodic oxidation.

3. The method of claim 1, wherein the electrolyte solution is selected from the group consisting of an alkali group electrolyte solution containing caustic soda, caustic potash, sodium hypochlorite, a neutral salt group electrolyte solution containing sodium chloride, potassium chloride, sodium bromide, potassium bromide, sodium nitrate, and a mixture including both said alkali group electrolyte solution and said neutral salt group electrolyte solution.

4. The method of claim 2, wherein the washing, cleaning and sterilizing solution is sprayed onto metal goods, fiber products or plastic goods to be cleaned, washed and sterilized.

5. The method of claim 2, wherein the washing, cleaning and sterilizing solution is injected into contaminated tanks, devices or fluid circulating pipes whereby to clean, wash and sterilize inner surfaces of the tanks, devices or fluid circulating pipes.

6. The method of claim 1, wherein, an electrolyzer is employed which includes:

an anode formed of a conductive metal which is covered with a conductive ceramics film, a vacuum-evaporated or flame-sprayed conductive ceramics film, or a diamond film which is made conductive and is vacuum-evaporated or flame-sprayed; and a cathode formed of a conductive metal.

7. The method of claim 6, wherein the metal is comprised of titanium or stainless steel.

8. A washing, cleaning and sterilizing system for cleaning, washing and sterilizing contaminated metal goods, fiber products, plastics goods or the like, wherein:

contaminated goods are immersed, cleaned, washed and sterilized in a washing bath or a washing machine filled with a washing/cleaning/sterilizing solution which is produced by electrolyzing an alkaline electrolyte solution having a pH value of 8 to 13 and comprising an alkali group electrolyte solution comprising caustic soda, caustic potash or sodium hypochlorite, or a neutral salt group electrolyte solution comprising sodium chloride, potassium chloride, sodium bromide or potassium bromide, or a solution including both said alkali group electrolyte solution and said neutral salt group electrolyte solution, the washing, cleaning and sterilizing solution being used as it is or diluted by tap water or non-potable water, and used washing, cleaning and sterilizing solution is returned to the electrolyzer where the solution is re-electrolyzed and contaminants contained therein decomposed by anodic oxidation.

9. The method of claim 1, wherein the solution has a pH of 10 to 12.3.

10. The system of claim 9, wherein the solution has a pH of 10 to 12.3.

* * * * *